United States Patent [19]

Marfat

[11] Patent Number: 6,040,329

[45] Date of Patent: Mar. 21, 2000

[54] SUBSTITUTED INDAZOLE ANALOGS

[75] Inventor: Anthony Marfat, Mystic, Conn.

[73] Assignee: Pfizer Inc, New York, N.Y.

[21] Appl. No.: 08/869,358

[22] Filed: Jun. 5, 1997

Related U.S. Application Data

[60] Provisional application No. 60/020,385, Jun. 25, 1996.

[51] Int. Cl.[7] .................. C07D 403/04; A61K 31/415
[52] U.S. Cl. ................ 514/405; 514/374; 514/406; 548/365.4
[58] Field of Search ............... 548/361.1; 514/406, 514/405

[56] References Cited

U.S. PATENT DOCUMENTS 5,444,038   8/1995   James et al. .................... 504/253

FOREIGN PATENT DOCUMENTS

| | | |
|---|---|---|
| 242167 | 10/1987 | European Pat. Off. . |
| 544218 | 6/1993 | European Pat. Off. . |
| 574174 | 12/1993 | European Pat. Off. . |
| 656359 | 6/1995 | European Pat. Off. . |
| 9219594 | 11/1992 | WIPO . |
| 9319749 | 10/1993 | WIPO . |
| 9612720 | 5/1996 | WIPO . |

OTHER PUBLICATIONS

Sutherland, et al., Pharmacol. Rev., 12(2), 265–299 (1960).
Beavo et al., TIPS, 11, 150–5 (1990).
Nicholson, et al., TIPS, 12, 19–27 (1991).
Verghese et al., J. Mol. Cell Cardiol., 21 (Suppl. II), (1989).
T.J. Torphy, Directions for New Anti–Asthma Drugs, 37–53, Birkhauser Verlag Basel (1988).
Kidney Int., 37:362 (1990).
W. Friers, Fed. of Euro. Bio. Soc. (FEBS) Letters, 285(2), 199–212 (1991).
Spooner et al., Clinical Immu–nology and Immunopathol––ogy, 62(1), S11–S17 (1992).
Dennler, Tetrahedron, 22(9), 3131–41 (Sep. 1996).
Ried, Justus Liegigs Annalen Der Chemie, 681, 45–51 (1965).
Sepulveda–Arques, Monats–Hefte Fur Chemie, 120(12), 1113–18 (1989).
Sugaya, Synthesis, 1, 73–6 (1994).
Chemical Abstracts, 95(22), 557, 195118 (1981).
Stafford and Feldman, Annual Reports in Medicinal Chem-is–try, Chapter 8, 71–80 (1996).
Dennler, et al., Tetrahedron, 22, pp. 3131–3141 (1966).

*Primary Examiner*—Alan L. Rotman
*Attorney, Agent, or Firm*—Peter C. Richardson; Paul H. Ginsburg; Raymond M. Speer

[57] ABSTRACT

The invention relates to compounds of the formula I

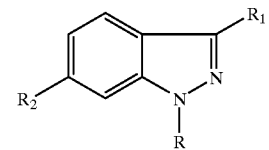

and pharmaceutically acceptable salts thereof, wherein R, $R_1$, and $R_2$, are as defined herein. The invention further relates to pharmaceutical compositions containing, and methods of using, the compounds of formula I, or acceptable salts thereof, for the inhibition of phosphodiesterase (PDE) type IV or the production of tumor necrosis factor (TNF) in a mammal.

12 Claims, No Drawings

SUBSTITUTED INDAZOLE ANALOGS

This application claims the benefit of Provisional Application Ser. No. 60/020,385, filed on Jun. 25, 1996.

This invention relates to novel indazole analogs. The compounds are selective inhibitors of phosphodiesterase (PDE) type IV and the production of tumor necrosis factor (TNF), and as such are useful in the treatment of asthma, arthritis, bronchitis, chronic obstructive airway disease, psoriasis, allergic rhinitis, dermatitis, and other inflammatory diseases, central nervous system disorders such as depression and multi-infarct dementia, AIDS, septic shock and other diseases involving the production of TNF. This invention also relates to a method of using such compounds in the treatment of the foregoing diseases in mammals, especially humans, and to pharmaceutical compositions containing such compounds.

Since the recognition that cyclic adenosine phosphate (AMP) is an intracellular second messenger (E. W. Sutherland, and T. W. Rall, *Pharmacol. Rev.*, 12, 265, (1960)), inhibition of the phosphodiesterases has been a target for modulation and, accordingly, therapeutic intervention in a range of disease processes. More recently, distinct classes of PDE have been recognized (J. A. Beavo et al., *Trends in Pharm. Sci.* (*TIPS*), 11, 150, (1990)), and their selective inhibition has led to improved drug therapy (C. D. Nicholson, M. S. Hahid, *TIPS*, 12, 19, (1991)). More particularly, it has been recognized that inhibition of PDE type IV can lead to inhibition of inflammatory mediator release (M. W. Verghese et al., *J. Mol. Cell Cardiol.*, 12 (Suppl. II), S 61, (1989)) and airway smooth muscle relaxation (T. J. Torphy in "Directions for New Anti-Asthma Drugs," eds S. R. O'Donnell and C. G. A. Persson, 1988, 37 Birkhauser-Verlag). Thus, compounds that inhibit PDE type IV, but which have poor activity against other PDE types, would inhibit the release of inflammatory mediators and relax airway smooth muscle without causing cardiovascular effects or antiplatelet effects. It has also been disclosed that PDE IV inhibitors are useful in the treatment of diabetes insipidus (Kidney Int. 37:362, 1990; Kidney Int. 35:494) and central nervous system disorders such as depression and multi-infarct dementia (PCT international application WO 92/19594 (published Nov. 12, 1992)).

TNF is recognized to be involved in many infectious and auto-immune diseases (W. Friers, *Fed. of Euro. Bio. Soc.* (*FEBS*) Letters, 285, 199, (1991)). Furthermore, it has been shown that TNF is the prime mediator of the inflammatory response seen in sepsis and septic shock (C. E. Spooner et al., Clinical Immunology and Immunopathology, 62, S11, (1992)).

SUMMARY OF THE INVENTION

The present invention relates to compounds of the formula I

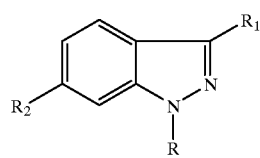

I and to pharmaceutically acceptable salts thereof, wherein:

R is H, $C_1$–$C_6$ alkyl, —$(CH_2)_m(C_3$–$C_7$ cycloalkyl), —$(CH_2)_m(C_3$–$C_9$ heterocyclyl), wherein m is 0 to 2, ($C_1$–$C_6$ alkoxy)$C_1$–$C_6$ alkyl, $C_2$–$C_6$ alkenyl, or —$(Z_1)_b(Z_2)_c(C_6$–$C_{10}$ aryl) wherein b and c are independently 0 or 1, $Z_1$ is $C_1$–$C_6$ alkylene or $C_2$–$C_6$ alkenylene, and $Z_2$ is O, S, $SO_2$, or $NR_{10}$, and wherein said R groups are optionally substituted by one or more substituents independently selected from the group consisting of halo, hydroxy, $C_1$–$C_5$ alkyl, $C_2$–$C_5$ alkenyl, $C_1$–$C_6$ alkoxy, $C_3$–$C_6$ cycloalkoxy, trifluoromethyl, nitro, —$CO_2R_{10}$, —$C(O)NR_{10}R_{11}$, —$NR_{10}R_{11}$ and —$SO_2NR_{10}R_{11}$;

$R_1$ is H, $C_1$–$C_7$ alkyl, $C_2$–$C_3$ alkenyl, phenyl, $C_3$–$C_7$ cycloalkyl, or ($C_3$–$C_7$ cycloalkyl)$C_1$–$C_2$ alkyl, wherein said alkyl, alkenyl and phenyl $R_1$ groups are optionally substituted by 1 to 3 substituents independently selected from the group consisting of methyl, ethyl, trifluoromethyl, and halo;

$R_2$ is 2-oxo-4-pyrrolyl, pyrazolyl, 2-oxo-3,4-dihydro-5-pyrimidyl, 2-oxo-3,4-dihydro-4-pyrimidyl, 2-oxo-tetrahydro-4-pyrimidyl, 2-oxo-tetrahydro-5-pyrimidyl, 2-oxo-4-pyrimidyl, or 2-oxo-5-pyrimidyl, wherein each of said $R_2$ groups is optionally substituted by 1 to 4 $R_6$ groups;

or $R_2$ is

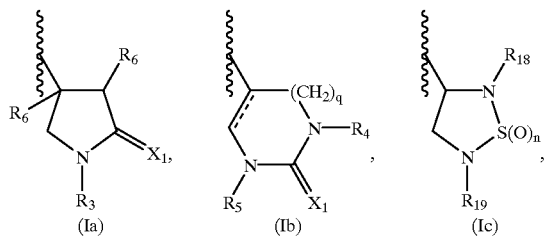

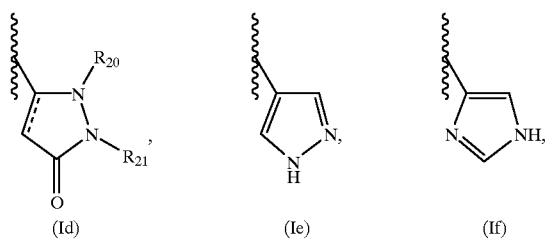

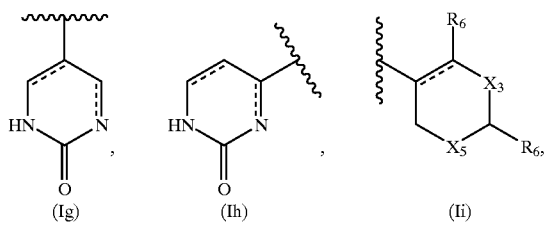

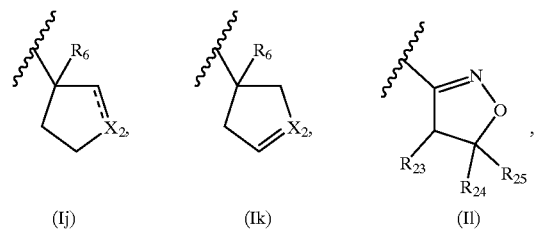

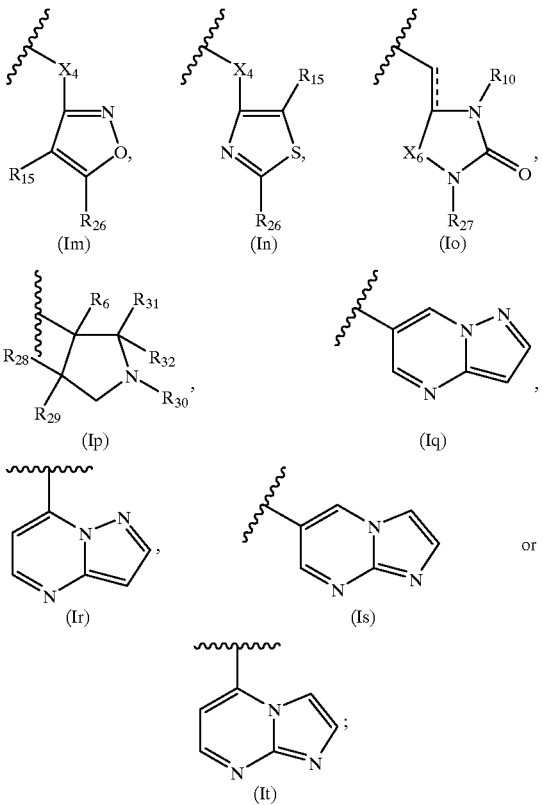

(Im) (In) (Io) (Ip) (Iq) (Ir) (Is) (It)

wherein, in said formulas (Ia)–(It), q is 0 or 1 in formula (Ib), n is 0 to 2 in formula (Ic), and the dashed lines appearing in formulas (Ib), (Id), (Ig), (Ih), (Ii), (Ij) and (Io) represent a double bond or a single bond;

$X_1$ is O or S;

$X_2$, in formula (Ik) and where the dashed line in formula (Ij) represents a double bond, is $CR_5$, $CR_6$, $CR_{16}$, or $COC(O)NR_9R_{12}$, or, where the dashed line in formula (Ij) represents a single bond, $X_2$ is $CR_5R_9$, $CR_6R_9$, or $CR_{16}R_9$;

$X_3$ is $C(=Z_3)$, C(S) or $CR_6R_{10}$;

$X_4$ is —$(CH_2)_m$— wherein m is 0 to 2;

$X_5$ is a bond or —$CH_2$—;

$X_6$ is —$CH_2$— or —C(O)—;

$R_3$ is H, hydroxy, $C_1$–$C_4$ alkoxy, —$CHR_7(O)_q(CH_2)_m$A wherein q is 0 or 1 and m is 0 to 2;

$R_4$ is H, hydroxy, $C_1$–$C_4$ alkyl, $C_1$–$C_2$ alkoxy, —OC(O)$CH_3$, $C_2$–$C_3$ alkenyl or (phenyl)$C_1$–$C_2$ alkyl;

$R_5$ is H, hydroxy, —$(CH_2)_m$A wherein m is 0 to 2, $C_1$–$C_6$ alkyl or $C_2$–$C_3$ alkanoyl, wherein said alkyl group is optionally substituted by 1 to 3 subtituents independently selected from halo, nitro, —$NR_{10}R_{11}$, —$CO_2R_{10}$, —$OR_{10}$, —OC(O)$R_{10}$, —C(O)$R_{10}$, cyano, —C(=Y)$NR_{10}R_{11}$, —$NR_{10}$C(=Y)$NR_{10}R_{11}$, —$NR_{10}$C(=Y)$R_{10}$, —$NR_{10}$C(O)$OR_{10}$, —C($NR_{10}$)$NR_{10}R_{11}$, —C(NCN)$NR_{10}R_{11}$, —C(NCN)$SR_{10}$, —$NR_{10}SO_2R_{10}$, —S(O)$_mR_{10}$ wherein m is 0 to 2, $NR_{10}SO_2CF_3$, —$NR_{10}$C(O)C(O)$NR_{10}R_{11}$, —$NR_{10}$C(O)C(O)$OR_{10}$, imidazolyl, and 1-(NH$R_{10}$)-2-imidazolyl;

each $R_6$ is independently selected from the group consisting of H, halo, cyano, $R_{13}$, cyclopropyl optionally substituted by $R_9$, —$OR_{10}$, —$CH_2OR_{10}$, —$NR_{10}R_{12}$, —$CH_2NR_{10}R_{12}$, —C(O)$OR_{10}$, —C(O)$NR_{10}R_{12}$, —CH=$CR_9R_9$, —C≡$CR_9$ and —C(=$Z_3$)H;

$R_7$ is H, —C(O)$R_8$, imidazolyl, pyrazolyl, triazolyl, tetrazolyl, oxazolyl, isoxazolyl, oxadiazolyl, thiadiazolyl, thiazolyl, oxazolidinyl, thiazolidinyl or imidazolidinyl;

each $R_8$ is independently —$OR_{10}$, —$NR_{10}R_{12}$ or $R_{13}$;

each $R_9$ is independently H, halo, or $C_1$–$C_4$ alkyl optionally substituted by 1 to 3 fluorines;

each $R_{10}$ and $R_{11}$ are independently selected from hydrogen and $C_1$–$C_4$ alkyl;

each $R_{12}$ is independently —$OR_{10}$ or $R_{10}$;

$R_{13}$ is $C_1$–$C_4$ alkyl;

each $R_{14}$ is independently selected from the group consisting of halo, nitro, cyano, —$NR_{10}R_{16}$, —$NR_{16}R_{12}$, —C(=$Z_3$)$R_8$, —S(O)$_mR_{13}$ wherein m is 0 to 2, —$OR_{12}$, —OC(O)$NR_{10}R_{12}$, —C($NR_{12}$)$NR_{10}R_{12}$, —C($NR_{10}$)$SR_{13}$, —OC(O)$CH_3$, —C(NCN)$NR_{10}R_{12}$, —C(S)$NR_{10}R_{12}$, —$NR_{12}$C(O)$R_{17}$, —C(O)$R_{17}$, oxazolyl, imidazolyl, thiazolyl, pyrazolyl, triazolyl and tetrazolyl;

each $R_{15}$ is independently hydrogen or $C_1$–$C_4$ alkyl optionally substituted by 1 to 3 fluorines;

each $R_{16}$ is independently H, $R_{13}$, —C(O)$R_{13}$, —C(O)C(O)$R_9$, —C(O)$NR_{10}R_{12}$, —S(O)$_mR_{13}$ wherein m is 0 to 2, —C(NCN)$SR_{13}$, —C(NCN)$R_{13}$, —C($NR_{12}$)$R_{13}$, —C($NR_{12}$)$SR_{13}$, or —C(NCN)$NR_{10}R_{12}$;

each $R_{17}$ is independently $R_{13}$, —C(O)$R_{13}$, oxazolidinyl, oxazolyl, thiazolyl, pyrazolyl, triazolyl, tetrazolyl, imidazolyl, imidazolidinyl, thiazolidinyl, isoxazolyl, oxadiazolyl, thiadiazolyl, morpholinyl, piperidinyl, piperazinyl or pyrrolyl wherein each of said $R_{17}$ heterocyclic groups is optionally substituted by one or two $C_1$–$C_2$ alkyl groups;

$R_{18}$ is H, $C_1$–$C_5$ alkyl, $C_2$–$C_5$ alkenyl, benzyl, or phenethyl;

$R_{19}$ is H, $C_1$–$C_5$ alkyl, $C_1$–$C_5$ alkanoyl, or benzoyl;

$R_{20}$ is H, $C_1$–$C_4$ alkyl, carboxy, aminocarbonyl, $C_1$–$C_6$ alkyl optionally substituted by carboxy, —$(CH_2)_mC(O)$ ($C_1$–$C_6$ alkoxy), or —$(CH_2)_m$($C_6$–$C_{10}$ aryl) wherein m is 0 to 2;

$R_{21}$ is H, $C_1$–$C_6$ alkyl, —C(=Y)$R_{22}$, —C(=Y)NH$R_{22}$, —C(O)$OR_{22}$, or —$(CH_2)_nX_7$(pyridyl) wherein n is 0 to 5 and $X_7$ is a bond or —CH=CH—, and wherein said pyridyl moiety is optionally substituted by halo;

$R_{22}$ is $C_1$–$C_6$ alkyl, $C_3$–$C_8$ cycloalkyl, —$(CH_2)_m$($C_6$–$C_{10}$ aryl) or —$(CH_2)_nX_7$(pyridyl) wherein n is 0 to 5 and $X_7$ is a bond or —CH=CH—, and wherein said pyridyl moiety is optionally substituted by halo;

$R_{23}$ is H, $R_{15}$, $C_1$–$C_3$ alkyl substituted by hydroxy, or ($C_1$–$C_3$ alkyoxy)$C_1$–$C_3$ alkyl;

$R_{24}$ is H, $R_{15}$, carboxy, ($C_1$–$C_3$ alkyoxy)$C_1$–$C_3$ alkyl, $C_3$–$C_7$ cycloalkyl or $C_1$–$C_5$ alkyl substituted by —$NR_{10}R_{11}$;

or $R_{23}$ and $R_{24}$ are taken together to form —$CH_2OCH_2OCH_2$—;

$R_{25}$ is H, hydroxy, $C_1$–$C_4$ alkyl optionally substituted by hydroxy, —C(O)$R_{10}$, —$NR_{10}R_{11}$, —$(CH_2)_mNHC(O)$ $R_{10}$, —$(CH_2)_mNHC(O)R_3$, —$(CH_2)_mCO_2R_{10}$, —$(CH_2)_mC(O)NR_{10}R_{11}$, —$(CH_2)_mC(O)N(OH)R_{10}$, —$(CH_2)_mSO_2NR_{10}R_{11}$, —$(CH_2)_mPO_3H_2$, —$(CH_2)_mSO_2NHC(O)R_{13}$ or —$(CH_2)_mSO_2NHC(O)$(phenyl), wherein m is 0 to 4;

$R_{26}$ is H, $C_1$–$C_4$ alkyl, phenyl, —$NR_{10}R_{11}$, or —$NR_{10}$ ($C_1$–$C_4$ alkanoyl);

$R_{27}$ is $R_{10}$, —$CH_2CO_2R_{13}$ or —$CH_2C(O)NR_{10}R_{11}$;

$R_{28}$ is —$C(O)R_{10}$, —$C(O)(C_6$–$C_{10}$ aryl), —$C(O)(C_3$–$C_9$ heteroaryl), —$CO_2R_{10}$, —$C(O)NR_{10}R_{11}$, cyano, nitro, —$CH_2OH$, —$NR_{10}SO_2R_{10}$, —$NHSO_2(C_6$–$C_{10}$ aryl), —$NHCO_2(C_1$–$C_4$ alkyl), —$NR_{10}C(O)R_{10}$ or —$NHCO_2(C_6$–$C_{10}$ aryl);

$R_{29}$ is $R_{15}$, cyano, carboxy, formyl, —$C(O)R_{10}$, or $C_1$–$C_4$ alkanoyl;

$R_{30}$ is cyano, —$NR_{10}R_{11}$, —$SO_2(C_1$–$C_4$ alkyl), —$SO_2(C_1$–$C_{10}$ aryl), —$C(O)R_{10}$, —$C(O)(C_6$–$C_{10}$ aryl), —$C(O)(C_3$–$C_9$ heteroaryl), —$C(O)NR_{10}R_{11}$, or —$CO_2R_{10}$;

$R_{31}$ and $R_{32}$ are each independently H, cyano, nitro, —$CO_2R_{10}$, —$C(O)NR_{10}R_{11}$, —$CH_2OH$, —$C(O)R_{10}$, —$NHCO_2R_{10}$, or —$NHSO_2R_{10}$;

A is pyridyl, morpholinyl, piperidinyl, imidazolyl, thienyl, pyrimidyl, thiazolyl, phenyl or naphthyl, wherein each of said A groups is optionally substituted by 1 or 2 $R_{14}$ groups or by 1 $R_{15}$ group;

$Z_3$ is O, $NR_{12}$, $NOR_{10}$, N(CN), $C(CN)_2$, $CR_{10}NO_2$, $CR_{10}C(O)OR_{13}$, $CR_{10}C(O)NR_{10}R_{11}$, $C(CN)NO_2$, $C(CN)C(O)OR_{13}$ or $C(CN)C(O)NR_{10}R_{11}$; and, Y is O or S.

Specific embodiments of the compounds of formula I include those wherein R is cyclopentyl or cyclohexyl, $R_1$ is $C_1$–$C_2$ alkyl, preferably ethyl, $R_2$ is a substituent of formula (Ia) wherein $X_1$ is O and $R_6$ and $R_3$ are both H.

Other specific embodiments of the compounds of formula I include those wherein R is cyclopentyl or cyclohexyl, R. is $C_1$–$C_2$ alkyl, preferably ethyl, $R_2$ is a substituent of formula (Ib) wherein $X_1$ is O, q is 1, the dashed line indicates a single bond, and $R_4$ and $R_5$ are both H.

Other specific embodiments of the compounds of formula I include those wherein R is cyclopentyl or cyclohexyl, $R_1$ is $C_1$–$C_2$ alkyl, preferably ethyl, $R_2$ is a substituent of formula (Id) wherein the dashed line indicates a single bond, $R_{20}$ is methyl and $R_{21}$ is H or —$C(O)NR_{10}R_{11}$.

Other specific embodiments of formula I include those compounds wherein R is cyclopentyl or cyclohexyl, $R_1$ is $C_1$–$C_2$ alkyl, preferably ethyl, $R_2$ is a moiety of formula (Io) wherein the dashed line represents a single bond, $X_6$ is —$CH_2$—, and $R_{10}$ and $R_{27}$ are both H.

Other specific embodiments of formula I include those compounds wherein R is cyclopentyl or cyclohexyl, $R_1$ is $C_1$–$C_2$ alkyl, preferably ethyl, $R_2$ is a moiety of formula (Ip) wherein $R_{31}$ and $R_{32}$ are both H, $R_{28}$ is —$C(O)R_{10}$, —$CO_2R_{10}$, —$C(O)(C_6$–$C_{10}$ aryl), cyano, nitro, —$C(O)NR_{10}R_{11}$, —$NR_{10}C(O)R_{10}$, or —$NR_{10}SO_2R_{10}$, $R_{29}$ is $R_{10}$ or —$C(O)R_{10}$, $R_6$ is H and $R_{30}$ is —$CO_2R_{10}$, cyano or —$C(O)R_{10}$. Other specific compounds within this group include those wherein $R_6$, $R_{31}$, and $R_{32}$ are H, $R_{30}$ is —$CO_2CH_3$, $R_{28}$ is —$C(O)CH_3$ and $R_{29}$ is —$CH_3$.

Other specific embodiments of the compounds of formula I include those wherein $R_2$ is a substituent of formula (Ic), (Ie), (If), (Ig), (Ih), (Ii), (Ij), (Ik), (Il), (Im), (In), (Iq), (Ir), (Is) or (It).

Specific preferred compounds include the following:
racemic 4-(1-Cyclopentyl-3-ethyl-1H-indazol-6-yl)-pyrrolidine-2-one;
(+)-4-(1-Cyclopentyl-3-ethyl-1H-indazol-6-yl)-pyrrolidine-2-one;
(−)-4-(1-Cyclopentyl-3-ethyl-1H-indazol-6-yl)-pyrrolidine-2-one;
and pharmaceutically acceptable salts of said compounds.

Other specific preferred compounds include the following:
racemic 4-(1-Cyclohexyl-3-ethyl-1H-indazol-6-yl)-pyrrolidine-2-one;
(+)4-(1-Cyclohexyl-3-ethyl-1H-indazol-6-yl)-pyrrolidine-2-one;
(−)-4-(1-Cyclohexyl-3-ethyl-1H-indazol-6-yl)-pyrrolidine-2-one;
and pharmaceutically acceptable salts of said compounds.

The present invention further relates to a pharmaceutical composition for the inhibition of phosphodiesterase (PDE) type IV or the production of tumor necrosis factor (TNF) comprising a pharmaceutically effective amount of a compound according to formula I, as defined above, or a pharmaceutically acceptable salt thereof, and a pharmaceutically acceptable carrier.

The present invention further relates to a method for the inhibition of phosphodiesterase (PDE) type IV or the production of tumor necrosis factor (TNF) by administering to a patient an effective amount of a compound according to formula I, as defined above, or a pharmaceutically acceptable salt thereof.

The present invention further relates to a pharmaceutical composition for the prevention or treatment of asthma, joint inflammation, rheumatoid arthritis, gouty arthritis, rheumatoid spondylitis, osteoarthritis, and other arthritic conditions; sepsis, septic shock, endotoxic shock, gram negative sepsis, toxic shock syndrome, acute respiratory distress syndrome, cerebal malaria, chronic pulmonary inflammatory disease, silicosis, pulmonary sarcoidosis, bone resorption diseases, reperfusion injury, graft vs. host reaction, allograft rejections, fever and myalgias due to infection, such as influenza, cachexia secondary to infection or malignancy, cachexia secondary to human acquired immune deficiency syndrome (AIDS), AIDS, HIV, ARC (AIDS related complex), keloid formation, scar tissue formation, Crohn's disease, ulcerative colitis, pyresis, multiple sclerosis, type 1 diabetes mellitus, diabetes insipidus, autoimmune diabetes, systemic lupus erythematosis, bronchitis, chronic obstructive airway disease, psoriasis, Bechet's disease, anaphylactoid purpura nephritis, chronic glomerulonephritis, inflammatory bowel disease, leukemia, allergic rhinitis, dermatitis, depression or multi-infarct dementia, comprising a pharmaceutically effective amount of a compound according to formula I, as defined above, or a pharmaceutically acceptable salt, thereof together with a pharmaceutically acceptable carrier.

This invention further relates to a method of treating or preventing the foregoing specific diseases and conditions by administering to a patient an effective amount of a compound according to formula I, as defined above, or a pharmaceutically acceptable salt thereof.

The term "halo", as used herein, unless otherwise indicated, means fluoro, chloro, bromo or iodo. Preferred halo groups are fluoro, chloro and bromo.

The term "alkyl", as used herein, unless otherwise indicated, includes saturated monovalent hydrocarbon radicals having straight, cyclic or branched moieties.

The term "alkoxy", as used herein, unless otherwise indicated, includes -O-alkyl groups wherein alkyl is as defined above.

The term "alkanoyl", as used herein, unless otherwise indicated, includes —C(O)-alkyl groups wherein alkyl is as defined above.

The term "cycloalkyl", as used herein, unless otherwise indicated, includes saturated monovalent cyclo hydrocarbon radicals including cyclobutyl, cyclopentyl and cycloheptyl.

The term "aryl", as used herein, unless otherwise indicated, includes an organic radical derived from an aromatic hydrocarbon by removal of one hydrogen, such as phenyl or naphthyl.

The term "heterocyclyl", as used herein, unless otherwise indicated, includes aromatic and non-aromatic heterocyclic groups containing one or more heteroatoms each selected from O, S and N. The heterocyclic groups include benzo-fused ring systems and ring systems substituted with an oxo moiety. An example of a $C_3$ heterocyclic group is thiazolyl, and an example of a $C_9$ heterocyclic group is quinolinyl. Examples of non-aromatic heterocyclic groups are pyrrolidinyl, piperidino, morpholino, thiomorpholino and piperazinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl and thiazolyl. Heterocyclic groups having a fused benzene ring include benzimidazolyl.

The term "heteroaryl", as used herein, unless otherwise indicated, includes aromatic heterocyclic groups wherein heterocyclic is as defined above.

The phrase "pharmaceutically acceptable salt(s)", as used herein, unless otherwise indicated, includes salts of acidic or basic groups which may be present in the compounds of formula I.

Certain compounds of formula I may have asymmetric centers and therefore exist in different enantiomeric forms. This invention relates to the use of all optical isomers and stereoisomers of the compounds of formula I and mixtures thereof. The compounds of formula I may also exist as tautomers. This invention relates to the use of all such tautomers and mixtures thereof.

DETAILED DESCRIPTION OF THE INVENTION

The following reaction schemes 1–3 illustrate the preparation of the compounds of the present invention. Unless otherwise indicated, R and $R^1$ in the reaction schemes are defined as above.

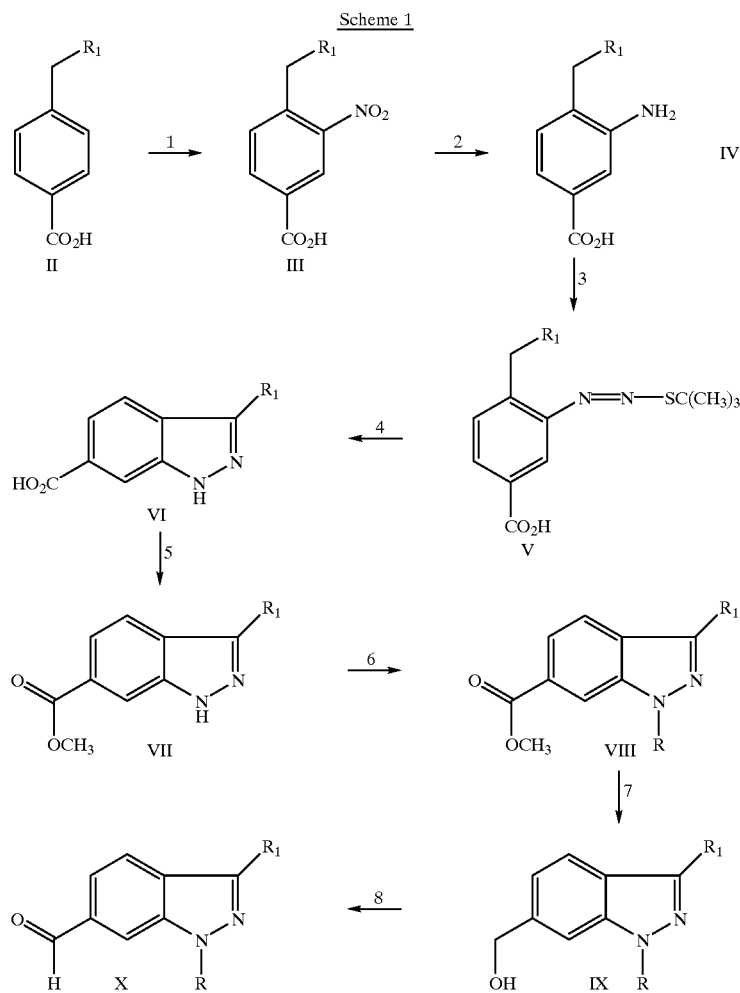

Scheme 2

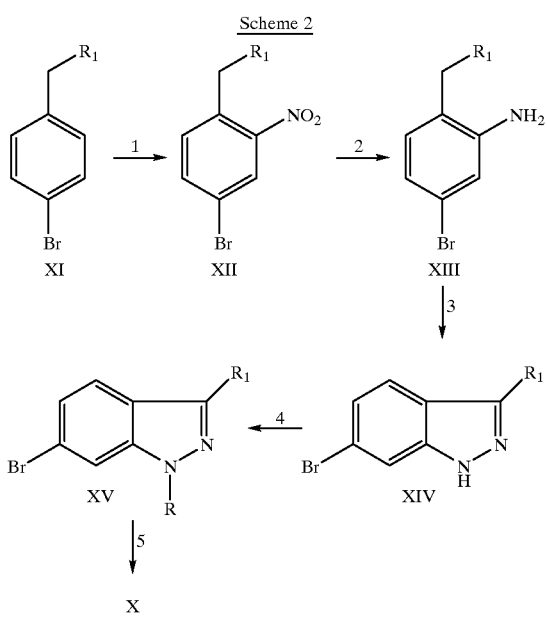

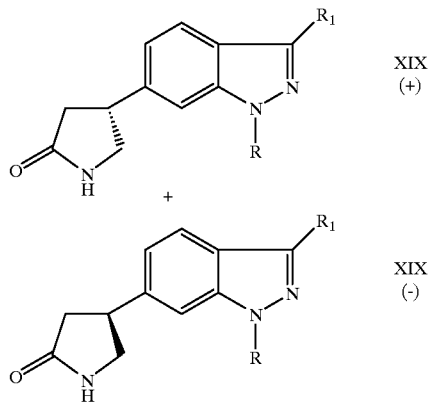

Scheme 3

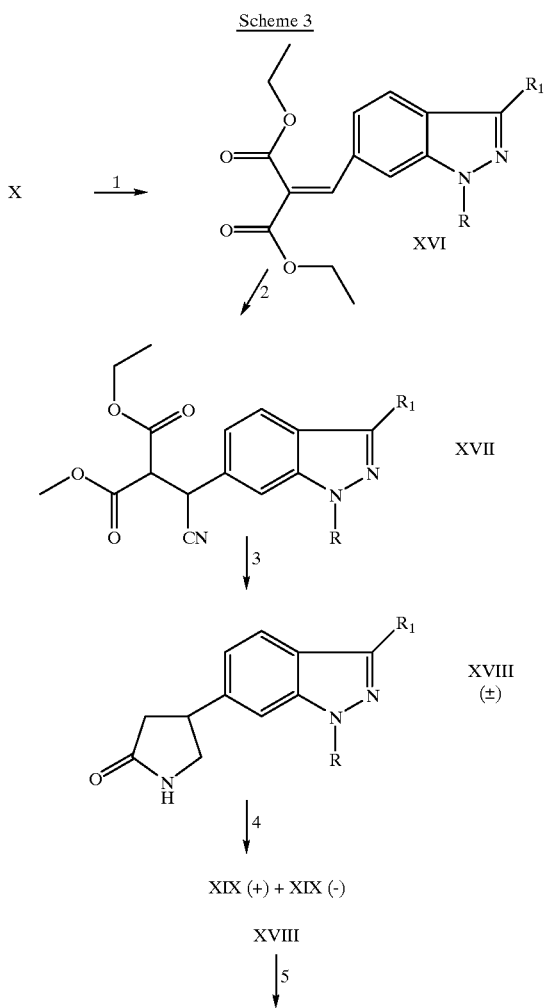

The preparation of compounds of formula I can be carried out by one skilled in the art according to one or more of the synthetic methods outlined in schemes 1–3 above and the examples referred to below. In step 1 of scheme 1, the carboxylic acid of formula II, which is available from known commercial sources or can be prepared according to methods known to those skilled in the art, is nitrated under standard conditions of nitration ($HNO_3/H_2SO_4$, 0° C.) and the resulting nitro derivative of formula III is hydrogenated in step 2 of scheme 1 using standard hydrogenation methods ($H_2$—Pd/C under pressure) at ambient temperature (20–25° C.) for several hours (2–10 hours) to provide the compound of formula IV. In step 3 of scheme 1, the amino benzoic acid of formula IV is reacted with a base such as sodium carbonate under aqueous conditions and gently heated until mostly dissolved. The reaction mixture is chilled to a lower temperature (about 0° C.) and treated with sodium nitrate in water. After about 15 minutes, the reaction mixture is slowly transferred to an appropriate container holding crushed ice and a strong acid such as hydrochloric acid. The reaction mixture is stirred for 10–20 minutes and then added, at ambient temperature, to a solution of excess t-butyl thiol in an aprotic solvent such as ethanol. The reaction mixture is acidified to a pH of 4–5 through addition of an inorganic base, preferably saturated aqueous $Na_2CO_3$, and the reaction mixture is allowed to stir at ambient temperature for 1–3 hours. Addition of brine to the reaction mixture, followed by filtration, provides the sulfide of formula V.

In step 4 of scheme 1, the sulfide of formula V is converted to the corresponding indazole carboxylic acid of formula VI by reacting the sulfide of formula V with a strong base, preferably potassium t-butoxide, in dimethyl sulfoxide (DMSO) at ambient temperature. After stirring for several hours (14 hours), the reaction mixture is acidified with a strong acid, such as hydrochloric or sulfuric acid, and then extracted using conventional methods. In step 5 of scheme 1, the indazole carboxylic acid of formula VI is converted to the corresponding ester of formula VII by conventional methods known to those skilled in the art. In step 6 of scheme 1, the compound of formula VIII is provided through alkylation of the ester of formula VII by subjecting the ester to conventional alkylation conditions (strong base/ various alkylating agents and, optionally, a copper catalyst such as $CuBr_2$) in a polar aprotic solvent, such as tetrahydrofuran (THF), N-methylpyrrolidinone or dimethylformamide (DMF), at ambient or higher temperature (25–200° C.) for about 6–24 hrs, preferably about 12 hours. In step 7 of scheme 1, the compound of formula VIII is converted to the corresponding alcohol of formula IX by following conventional methods known to those skilled in the art for reducing esters to alcohols. Preferably, the reduction is effected through use of a metal hydride reducing agent, such as lithium aluminum hydride, in a polar aproptic solvent at a low temperature (about 0° C.). In step 8 of scheme 1, the alcohol of formula IX is oxidized to the corresponding aldehyde of formula X according to conventional methods known to those skilled in the art. For example, the oxidation can be effected through use of a catalytic amount of tetrapropylammonium perrutenate and excess N-methylmorpholine-N-oxide, as described in J. Chem. Soc., Chem. Commun., 1625 (1987), in an anhydrous solvent, preferably methylene chloride.

Scheme 2 provides an alternative method of preparing the aldehyde of formula X. In step 1 of scheme 2, the compound of formula XI is nitrated using conventional nitration conditions (nitric and sulfuric acid) to provide the compound of formula XII. In step 2 of scheme 2, the nitro derivative of formula XII is reduced to the corresponding amine of formula XIII according to conventional methods known to those skilled in the art. Preferably, the compound of formula XII is reduced to the amine of formula XIII using anhydrous stannous chloride in an anhydrous aprotic solvent such as ethanol. In step 3 of scheme 2, the amine of formula XIII is converted to the corresponding indazole of formula XIV by preparing the corresponding diazonium tetrafluoroborates as described in A. Roe, *Organic Reactions, Vol.* 5, Wiley, New York, 1949, pp. 198–206, followed by phase transfer catalyzed cyclization as described in R. A. Bartsch and I. W. Yang, J. Het. Chem. 21, 1063 (1984). In step 4 of scheme 2, alkylation of the compound of formula XIV is performed using standard methods known to those skilled in the art (i.e. strong base, polar aprotic solvent and an alkyl halide) to provide the N-alkylated compound of formula XV. In step 5 of scheme 2, the compound of formula XV is subjected to metal halogen exchange employing an alkyl lithium, such as n-butyl lithium, in a polar aprotic solvent, such as THF, at low temperature (–50° C. to 100° C. (–78° C. preferred)) followed by quenching with DMF at low temperature and warming to ambient temperature to provide the aldehyde intermediate of formula X.

Scheme 3 illustrates the preparation of compounds of formula I wherein R and $R_1$ are as defined above and $R_2$ is a substituent of formula (Ia) and $X_1$ is O. In step 1 of Scheme 3, aldehyde intermediate X is reacted in a polar anhydrous solvent, such as toluene, with diethylmalonate in the presence of an organic base, such as piperidine. The reaction mixture is heated to reflux and water that is produced during the reaction is collected using a Dean-Stark trap. The reaction is run for about 12–30 hours to provide the malonic acid diethyl ester intermediate XVI.

In step 2 of Scheme 3, the malonic acid diethyl ester intermediate XVI is treated with one equivalent of sodium cyanide at ambient temperature (20–25° C.) in an anhydrous polar solvent, such as ethanol, to provide, after acidic work up, the cyano intermediate XVII. In step 3 of Scheme 3, the cyano intermediate XVII is cyclized to pyrrolidin-2-one derivative XVIII by following a four step procedure. First, the cyano intermediate XVII is hydrogenated at high pressure (20–50 psi) using a metal catalyst, such as platinum, and an acidic solvent, such as acetic acid. Second, the intermediate from the first step is heated to reflux in the presence of an organic base, such as triethylamine, in an aprotic organic solvent, such as toluene, for about 10–24 hours. Third, the intermediate from the second step is treated with a strong base, such as sodium hydroxide, in a polar protic solvent, such as an alcohol, preferably ethanol, and heated to reflux for about 30 minutes to an hour. Fourth, the intermediate from the third step is heated to a high temperature, preferably 150–200° C., under an inert atmosphere for 15–30 minutes or until all bubbling has ceased. The crude product can be purified to provide the pyrrolidin-2-one derivative XVIII using standard chromatographic methods known to those skilled in art.

The pyrrolidin-2-one derivative XVIII is racemic and can be separated (or resolved) to its corresponding individual enantiomers using separation techniques known to those skilled in the art. Such methods are described in J. March, *Advanced Organic Chemistry*, (4th Edition, J. Wiley & Sons), 1992, pages 118–125. In step 4 of Scheme 3, such a resolution is accomplished using a chiral HPLC resolution method as described in Example 2, referred to below.

The compounds of formula I can also be prepared following one or more synthetic methods that are disclosed in published patent applications or issued patents. In particular, using the intermediates described in Schemes 1–3, referred to above, in particular the intermediates of formulas VIII, X, XV and XVIII, those skilled in the art can prepare the compounds of formula I using analogous synthetic methods that have been described for compounds in which a phenyl ring is substituted for the indazole ring in the compounds of formula I. Such analogous synthetic methods are disclosed in U.S. Pat. No. 5,270,206 (issued Dec. 14, 1993) and the following published patent applications: EP 428313 (published Feb. 2, 1994); EP 511865 (published Nov. 4, 1992); EP 671389 (published Mar. 30, 1995); Japanese published application no. 7215952 (published Aug. 15, 1995); Japanese published application no. 7017952 (published Jan. 20, 1995); PCT application WO 87/06576 (published Nov. 5, 1987); PCT application WO 91/07178 (published May 30, 1991); PCT application 91/15451 (published Oct. 17, 1991); PCT application WO 91/16303 (published Oct. 31, 1991); PCT application WO 92/07567 (published May 14, 1992); PCT application 92/19594 (published Nov. 12, 1992); PCT application 93/07111 (published Apr. 15, 1993); PCT application WO 93/07141 (published May 15, 1993); PCT application 94/12461 (published Jun. 9, 1994); PCT application WO 95/08534 (published Mar. 30, 1995); PCT application WO 95/14680 (published Jun. 1, 1995); and PCT application WO 95/14681 (Jun. 1, 1995). The foregoing United States patent and each of the foregoing published patent applications are incorporated herein by reference in their entirety. Each of the foregoing published PCT applications designates the United States.

Specifically, the compounds of formula I wherein $R_2$ is 2-oxo-4-pyrrolyl, pyrazolyl, 2-oxo-3,4-dihydro-5-pyrimidyl, 2-oxo-3,4-dihydro-4-pyrimidyl, 2-oxo-tetrahydro-4-pyrimidyl, 2-oxo-tetrahydro-5-pyrimidyl, 2-oxo-4-pyrimidyl, or 2-oxo-5-pyrimidyl can be prepared by following analogous synthetic methods disclosed in WO 87/06576, which is referred to above. The compounds of formula I wherein $R_2$ is a substituent of formula (Ia) can be prepared by following analogous synthetic methods disclosed in WO 87/06576, WO 91/16303, WO 94/12461, WO 92/19594, or WO 93/07141, each of which is referred to above. The compounds of formula I wherein $R_2$ is a substituent of formula (Ib) can be prepared by following analogous synthetic methods disclosed in WO 87/06576, U.S. Pat. No. 5,270,206, WO 94/12461, WO 92/17567, WO 91/07178, or EP 428313, each of which is referred to above. The compounds of formula I wherein $R_2$ is a substituent of formula (Ic) can be prepared by following analogous synthetic methods disclosed in WO 87/06576, referred to above.

The compounds of formula I wherein $R_2$ is a substituent of formula (Id) can be prepared by following analogous synthetic methods disclosed in EP 511865, referred to above. The compounds of formula I wherein $R_2$ is a substituent of formula (Ie) or (If) can be prepared by following analogous synthetic methods disclosed in WO 87/06576 or WO 94/12461, each of which is referred to above. The compounds of formula I wherein $R_2$ is a substituent of formula (Ig) or (Ih) can be prepared by following analogous synthetic methods disclosed in WO 87/06576, which is referred to above. The compounds of formula I wherein $R_2$ is a substituent of formula (Ii) can be prepared by following analogous synthetic methods disclosed in WO 91/15451 or WO 93/07111, each of which is referred to above. The compounds of formula I wherein $R_2$ is a substituent of formula (Ij) or (Ik) can be prepared by following analogous synthetic methods disclosed in WO 93/07111, which is referred to above. The compounds of formula I wherein $R_2$ is a substituent of formula (Il) can be prepared by following analogous synthetic methods disclosed in WO 95/14680 or WO 95/14681, each of which is referred to above. The compounds of formula I wherein $R_2$ is a substituent of formula (Im) or (In) can be prepared by following analogous synthetic methods disclosed in Japanese published application no.7215952, which is referred to above. The compounds of formula I wherein $R_2$ is a substituent of formula (Io) can be prepared by following analogous synthetic methods disclosed in Japanese published application no. 7017952, which is referred to above. The compounds of formula I wherein $R_2$ is a substituent of formula (Ip) can be prepared by following analogous synthetic methods disclosed in WO 95/08534 or EP 671389, each of which is referred to above. The compounds of formula I wherein $R_2$ is a substituent of formula (Iq), (Ir), (Is), or (It) can be prepared by following analogous synthetic methods disclosed in WO 87/06576, which is referred to above.

The compounds of formula I that are basic in nature are capable of forming a wide variety of different salts with various inorganic and organic acids. Although such salts must be pharmaceutically acceptable for administration to animals, it is often desirable in practice to initially isolate the compound of formula I from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent, such as methanol or ethanol. Upon evaporation of the solvent, the desired solid salt is readily obtained. The desired acid addition salt can also be precipitated from a solution of the free base in an organic solvent by adding to the solution an appropriate mineral or organic acid. Cationic salts of the compounds of formula I are similarly prepared except through reaction of a carboxy group, such as where $R_{24}$ is carboxy, with an appropriate cationic salt reagent such as sodium, potassium, calcium, magnesium, ammonium, N,N'-dibenzylethylenediamine, N-methylglucamine (meglumine), ethanolamine, tromethamine, or diethanolamine.

For administration to humans in the curative or prophylactic treatment of inflammatory diseases, oral dosages of a compound of formula I or a pharmaceutically acceptable salt thereof (the active compounds) are generally in the range of 0.1 to 1000 mg daily for an average adult patient (70 kg), in single or divided doses. The active compounds can be administered in single or divided doses. Individual tablets or capsules should generally contain from 0.1 to 100 mg of active compound, in a suitable pharmaceutically acceptable vehicle or carrier. Dosages for intravenous administration are typically within the range of 0.1 to 10 mg per single dose as required. For intranasal or inhaler administration, the dosage is generally formulated as a 0.1 to 1% (w/v) solution. In practice the physician will determine the actual dosage which will be most suitable for an individual patient and it will vary with the age, weight and response of the particular patient. The above dosages are exemplary of the average case but there can, of course, be individual instances where higher or lower dosage ranges are merited, and all such dosages are within the scope of this invention.

For administration to humans for the inhibition of TNF, a variety of conventional routes may be used including orally, parenterally, topically, and rectally (suppositories). In general, the active compound will be administered orally or parenterally at dosages between about 0.1 and 25 mg/kg body weight of the subject to be treated per day, preferably from about 0.3 to 5 mg/kg, in single or divided doses. However, some variation in dosage will necessarily occur depending on the condition of the subject being treated. The person responsible for administration will, in any event, determine the appropriate dose for the individual subject.

For human use, the active compounds of the present invention can be administered alone, but will generally be administered in an admixture with a pharmaceutical diluent or carrier selected with regard to the intended route of administration and standard pharmaceutical practice. For example, they may be administered orally in the form of tablets containing such excipients as starch or lactose, or in capsules either alone or in admixture with excipients, or in the form of elixirs or suspensions containing flavoring or coloring agents. They may be injected parenterally; for example, intravenously, intramuscularly or subcutaneously. For parenteral administration, they are best used in the form of a sterile aqueous solution which may contain other substance; for example, enough salts or glucose to make the solution isotonic.

Additionally, the active compounds may be administered topically when treating inflammatory conditions of the skin and this may be done by way of creams, jellies, gels, pastes, and ointments, in accordance with standard pharmaceutical practice.

The therapeutic compounds may also be administered to a mammal other than a human. The dosage to be administered to a mammal will depend on the animal species and the disease or disorder being treated. The therapeutic compounds may be administered to animals in the form of a capsule, bolus, tablet or liquid drench. The therapeutic compounds may also be administered to animals by injection or as an implant. Such formulations are prepared in a conventional manner in accordance with standard veterinary practice. As an alternative the therapeutic compounds may be administered with the animal feedstuff and for this purpose a concentrated feed additive or premix may be prepared for mixing with the normal animal feed.

The ability of the compounds of formula I or the pharmaceutically acceptable salts thereof to inhibit PDE IV may be determined by the following assay.

Thirty to forty grams of human lung tissue is placed in 50 ml of pH 7.4 Tris/phenylmethylsulfonyl fluoride (PMSF)/ sucrose buffer and homogenized using a Tekmar Tissumizer® (Tekmar Co., 7143 Kemper Road, Cincinnati, Ohio 45249) at full speed for 30 seconds. The homogenate is centrifuged at 48,000× g for 70 minutes at 4° C. The supernatant is filtered twice through a 0.22 μm filter and applied to a Mono-Q FPLC column (Pharmacia LKB Biotechnology, 800 Centennial Avenue, Piscataway, N.J. 08854) pre-equilibrated with pH 7.4 Tris/PMSF Buffer. A flow rate of 1 ml/minute is used to apply the sample to the column, followed by a 2 ml/minute flow rate for subsequent washing and elution. Sample is eluted using an increasing, step-wise NaCl gradient in the pH 7.4 Tris/PMSF buffer. Eight ml fractions are collected. Fractions are assayed for specific $PDE_{IV}$ activity determined by [$^3$H]cAMP hydrolysis and the ability of a known $PDE_{IV}$ inhibitor (e.g. rolipram) to inhibit that hydrolysis. Appropriate fractions are pooled, diluted with ethylene glycol (2 ml ethylene glycol/5 ml of enzyme prep) and stored at −20° C. until use.

Compounds are dissolved in dimethylsulfoxide (DMSO) at a concentration of 10 mM and diluted 1:25 in water (400 μM compound, 4% DMSO). Further serial dilutions are made in 4% DMSO to achieve desired concentrations. The final DMSO concentration in the assay tube is 1%. In duplicate the following are added, in order, to a 12×75 mm glass tube (all concentrations are given as the final concentrations in the assay tube).

i) 25 μl compound or DMSO (1%, for control and blank)
ii) 25 μl pH 7.5 Tris buffer
iii) [$^3$H]cAMP (1 μM)
iv) 25 μl PDE IV enzyme (for blank, enzyme is preincubated in boiling water for 5 minutes)

The reaction tubes are shaken and placed in a water bath (37° C.) for 20 minutes, at which time the reaction is stopped by placing the tubes in a boiling water bath for 4 minutes. Washing buffer (0.5 ml, 0.1M 4-(2-hydroxyethyl)-1-piperazine-ethanesulfonic acid (HEPES)/0.1 M naci, pH 8.5) is added to each tube on an ice bath. The contents of each tube are filed to an AFF-Gel 601 column (Biorad Laboratories, P.O. Box 1229, 85A Marcus Drive, Melvile, N.Y. 11747) (boronate affinity gel, 1 ml bed volume) previously equilibrated with washing buffer. [$^3$H]cAMP is washed with 2×6 ml washing buffer, and [$^3$H]5'AMP is then eluted with 4 ml of 0.25M acetic acid. After vortexing, 1 ml of the elution is added to 3 ml scintillation fluid in a suitable vial, vortexed and counted for [$^3$H].

$$\% \text{ inhibition} = 1 - \frac{\text{average cpm (test compound} - \text{average cmp (blank)}}{\text{average cpm (control)} - \text{average cpm (blank)}}$$

$IC_{50}$ is defined as that concentration of compound which inhibits 50% of specific hydrolysis of [$^3$H]cAMP to [$^3$H] 5'AMP.

The ability of the compounds I or the pharmaceutically acceptable salts thereof to inhibit the production TNF and, consequently, demonstrate their effectiveness for treating disease involving the production of TNF is shown by the following in vitro assay:

Peripheral blood (100 mis) from human volunteers is collected in ethylenediaminetetraacetic acid (EDTA). Mononuclear cells are isolated by FICOLL/Hypaque and washed three times in incomplete HBSS. Cells are resuspended in a final concentration of 1×10$^6$ cells per ml in pre-warmed RPMI (containing 5% FCS, glutamine, pen/step and nystatin). Monocytes are plated as 1×10$^6$ cells in 1.0 ml in 24-well plates. The cells are incubated at 37° C. (5% carbon dioxide) and allowed to adhere to the plates for 2 hours, after which time non-adherent cells are removed by gentle washing. Test compounds (10 μl) are then added to the cells at 3–4 concentrations each and incubated for 1 hour. UPS (10 μl) is added to appropriate wells. Plates are incubated overnight (18 hrs) at 37° C. At the end of the incubation period TNF was analyzed by a sandwich ELISA (R&D Quantikine Kit). $IC_{50}$ determinations are made for each compound based on linear regression analysis.

The following Examples illustrate the invention.

PREPARATION 1

1-Cyclopentyl-3-ethyl-1H-indazole-6-carboxylic acid methyl ester

A. 3-Nitro-4-propyl-benzoic acid. 9.44 g (57.5 mmol, 1.0 equiv) of 4-propylbenzoic acid were partially dissolved in 50 mL concentrated $H_2SO_4$ and chilled in an ice bath. A solution of 4.7 mL (74.7 mmol, 1.3 equiv) concentrated $HNO_3$ in 10 mL concentrated $H_2SO_4$ was added dropwise over 1–2 min. After stirring 1 hour at 0° C., the reaction mixture was poured into a 1 L beaker half full with ice. After stirring 10 min., the white solid that formed was filtered, washed 1× $H_2O$, and dried to give 12.01 g (100%) of the title compound: mp 106–109° C.; IR (KBr) 3200–3400, 2966, 2875, 2667, 2554, 1706, 1618, 1537, 1299, 921 cm$^{-1}$; $^1$H NMR (300 MHz, DMSO-d$_6$) δ 0.90 (t, 3H J=7.4 Hz), 1.59 (m, 2H), 2.82 (m, 2H), 7.63 (d, 1H, J=8.0 Hz), 8.12 (dd, 1H, J=1.7, 8.0 Hz), 8.33 (d, 1H, J=1.7 Hz); $^{13}$C NMR (75.5 MHz, DMSO-d$_6$) δ 14.2, 23.7, 34.2, 125.4, 130.5, 132.9, 133.6, 141.4, 149.5, 165.9; Anal. calcd for $C_{10}H_{11}NO_4 \cdot \frac{1}{4}H_2O$: C, 56.20; H, 5.42; N, 6.55. Found: C, 56.12; H, 5.31; N, 6.81.

B. 3-Amino-4-propyl-benzoic acid. A mixture of 11.96 g (57.2 mmol) 3-nitro-4-propyl-benzoic acid and 1.5 g 10% Pd/C, 50% water wet, in 250 mL $CH_3OH$ was placed on a Parr hydrogenation apparatus and shaken under 25 psi $H_2$ at ambient temperature (20–25° C.). After 1 hours, the reaction mixture was filtered through Celite®, and the filtrate concentrated and dried to give 9.80 g (96%) of a pale yellow crystalline solid: mp 139.5–142.5° C.; IR (KBr) 3200–2400, 3369, 3298, 2969, 2874, 2588, 1690, 1426, 1260, 916, 864 cm$^{-1}$; $^1$H NMR (300 MHz, DMSO-d$_6$) δ 0.90 (t, 3H, J=7.2 Hz), 1.52 (m, 2H), 2.42 (m, 2H), 5.08 (br s, 2H), 6.96 (d, 1H, J=7.8 Hz), 7.05 (dd, 1H, J=1.7, 7.8 Hz), 7.20 (d, 1H, J=1.7 Hz), MS (Cl, $NH_3$) m/z 180 (M+H$^+$, base); Anal. calcd for $C_{10}H_{13}NO_2 \cdot \frac{1}{3}H_2O$: C, 64.85; N, 7.89; N, 7.56. Found: C, 64.69; H, 7.49; N, 7.86.

C. 3-Carboxy-6-propyl-benzenediazo t-butyl sulfide. A mixture of 8.80 g (49.1 mmol, 1.0 equiv) 3-amino-4-propyl-benzoic acid and 2.34 g (22.1 mmol, 0.45 quiv) sodium carbonate in 55 mL $H_2O$ was heated gently with a heat gun until mostly dissolved. The reaction mixture was chilled in an ice bath, and a solution of 3.73 g (54.0 mmol, 1.0 equiv) sodium nitrite in 27 mL $H_2O$ was added dropwise. After 15 minutes, the reaction mixture was transferred to a dropping funnel and added over 10 minutes to a beaker containing 55 g of crushed ice and 10.6 mL concentrated HCl. After stirring 10 minutes, the contents of the beaker were transferred to a dropping funnel and added over 5 minutes to a room temperature solution of 5.31 mL (47.1 mmol, 0.96 equiv) t-butyl thiol in 130 mL ethanol. The pH was adjusted to 4–5 by addition of saturated aqueous $Na_2CO_3$ solution, and the reaction mixture was allowed to stir 1 hour at ambient temperature (20–25° C.). 200 mL brine were added, and the mixture was filtered. The solid was washed 1× $H_2O$ and dried overnight to give 12.25 g (89%) of a brown/rust colored powder (caution-stench): mp 102° C. (dec); IR (KBr) 3200–2400, 2962, 2872, 2550, 1678, 1484, 1428, 1298, 1171 cm$^{-1}$; $^1$H NMR (300 MHz, DMSO-d$_6$) δ 0.84 (t, 3H, J=7.3 Hz), 1.48 (m, 2H), 1.55 (s, 9H), 2.42 (m, 2H), 7.29 (d, 1H, J=1.6 Hz), 7.50 (d, 1H, J=8.0 Hz), 7.86 (dd, 1H, J=1.7, 7.9 Hz), 13.18 (br s, 1H); MS (thermospray, NH$_4$OAc) m/z 281 (M+H+, base); Anal. calcd for C$_{14}$H$_{20}$N$_2$O$_2$S: C, 59.96; H, 7.19; N, 9.99. Found: C, 59.71; H, 7.32; N, 10.02.

D. 3-Ethyl-1H-indazole-6-carboxylic acid. A solution of 12.0 g (42.8 mmol, 1.0 equiv) 3-carboxy-6-propyl-benzenediazo t-butyl sulfide in 150 mL DMSO was added dropwise over 15 minutes to an ambient temperature solution of 44.6 g (398 mmol, 9.3 equiv) potassium t-butoxide in 200 mL dimethylsulfoxide (DMSO). After stirring 2 hours at ambient temperature, the reaction mixture was poured into 1.5 L of 0° C. 1N HCl, stirred 5 minutes, then extracted 2×350 mL ethyl acetate. The ethyl acetate extracts (caution-stench) were combined, washed 2×250 mL H$_2$O, and dried over MgSO$_4$. Filtration, concentration of filtrate and drying gave a tan solid, which was triturated with 1 L of 1:3 Et$_2$O/Hexanes and dried to give 7.08 g (87%) of a tan crystalline powder: mp 248–251° C.; IR (KBr) 3301, 3300–2400, 2973, 2504, 1702, 1455, 1401, 1219 cm$^{-1}$; $^1$H NMR (300 MHz, DMSO-d$_6$) δ 1.31 (t, 3H, J=7.6 Hz), 2.94 (q, 2H, J=7.6 Hz), 7.63 (dd, 1H, J=1.1, 8.4 Hz), 7.81 (d, 1H, J=8.4 Hz), 8.06 (d, 1H, J=1.1. Hz), 12.95 (br s, 1H); MS (Cl, NH$_3$) m/z 191 (M+H+, base); Anal. calcd for C$_{10}$H$_{10}$N$_2$O$_2$: C, 63.14; H, 5.30; N, 14.73. Found: C, 62.66; H, 5.42; N, 14.80.

E. 3-Ethyl-1H-indazole-6-carboxylic acid methyl ester. 8.78 g (45.8 mmol, 1.1 equiv) 1-(3-dimethylaminopropyl)-3-ethylcarbodiimide hydrochloride were added in one portion to an ambient temperature solution of 7.92 g (41.6 mmol, 1.0 equiv) 3-ethyl-1H-indazole-6-carboxylic acid, 16.9 mL (416 mmol, 10 equiv) methanol and 5.59 g (45.8 mmol, 1.1 equiv) dimethylaminopyridine (DMAP) in 250 mL CH$_2$Cl$_2$. After 18 hours at room temperature, the reaction mixture was concentrated to 150 mL, diluted with 500 mL ethyl acetate, washed 2×100 mL 1N HCl, 1×100 mL H$_2$O, 1×100 mL brine, and dried over Na$_2$SO$_4$. Filtration, concentration of filtrate and drying gave 7.8 g of a brown solid, which was purified on a silica gel column (30% to 50% ethyl acetate/hexane gradient) to give 6.41 g (75%) of a tan solid: mp 107–1080C; IR (KBr) 3100–2950, 1723, 1222 cm$^{-1}$; $^1$H NMR (300 MHz, CDCl$_3$) δ 8.19 (m, 1H), 7.7–7.8 (m, 2H), 3.96 (s, 3H), 3.05 (q, 2H, J=7.7 Hz), 1.43 (t, 3H, 7.7 Hz); MS (Cl, NH$_3$) m/z 205 (M+H$^+$, base); Anal. calcd for C$_{11}$H$_{12}$N$_2$O$_2$: C, 64.70; H, 5.92; N, 13.72. Found: C, 64.88; H, 6.01; N, 13.96.

F. 1-Cyclopentyl-3-ethyl-1H-indazole-6-carboxylic acid methyl ester. 1.17 g (29.4 mmol, 1.05 equiv) sodium hydride, 60% oil dispersion, were added in one portion to an ambient temperature solution of 5.7 g (27.9 mmol, 1.0 equiv) 3-ethyl-1H-indazole-6-carboxylic acid methyl ester in 125 mL anhydrous DMF. After 20 min., 3.89 mL (36.6 mmol, 1.3 equiv) cyclopentyl bromide were added dropwise, and the reaction mixture allowed to stir overnight at room temperature. The mixture was then poured into 1 L H$_2$O and extracted 3×450 mL ethyl acetate. The organic extracts were combined, washed 3×400 mL H$_2$O, 1×200 mL brine, and dried over Na$_2$SO$_4$. Filtration, concentration of filtrate and drying gave an amber oil, which was purified on a silica gel column (10% ethyl acetate/hexanes, gravity) to give 5.48 g (72%) of a clear oil: $^1$H NMR (300 MHz, CDCl$_3$) δ 8.16 (d, 1H, J=1.0 Hz), 7.7 (m, 2H), 5.00 (quintet, 1H, J=7.5 Hz), 3.97 (s, 3H), 3.01 (q, 2H, J=7.6 Hz), 2.2 (m, 4H), 2.0 (m, 2H), 1.8 (m, 2H), 1.39 (t, 3H, J=7.6 Hz); HRMS calcd for C$_{16}$H$_{20}$N$_2$O$_2$: 272.1526. Found: 272.15078.

G. (1-Cyclopentyl-3-ethyl-1H-indazol-6-yl)-methanol. 7 ml (7.0 mmol, 1.0 equiv) lithium aluminum hydride, 1.0 M solution in THF, were added to a 0° C. solution of 1.02 g (7.05 mmol, 1.0 equiv) 1-cyclopentyl-3-ethyl-1H-indazole-6-carboxylic acid methyl ester in 50 mL anhydrous THF. After 20 minutes, 1 mL methanol was added cautiously, then the reaction mixture was poured into 500 mL of 5% H$_2$SO$_4$ and extracted 3×50 mL ethyl acetate. The organic extracts were combined, washed 2×40 mL H$_2$O, 1×40 mL brine, and dried over Na$_2$SO$_4$. Filtration, concentration of filtrate, and drying gave 1.58 g of a clear oil, which was purified on a silica gel column to give 1.53 g (89%) clear oil: IR (CHCl$_3$) 3606, 3411, 3009, 2972, 2875, 1621, 1490 cm$^{-1}$; $^1$H NMR (300 Mhz, CDCl$_3$) δ 7.65 (d, 1H, J=8.0 Hz) 7.42 (s, 1H), 7.06 (dd, 1H, J=1.0, 8.2 Hz), 4.92 (quintet, 1H, J=7.7 Hz), 4.84 (s, 2H), 2.98 (q, 2H, J=7.6 Hz), 2.2 (m, 4H), 2.0 (m, 2H), 1.7 (m, 3H), 1.38 (t, 3H, J=7.6 Hz); MS (thermospray, NH$_4$OAc) m/z 245 (M+H$^+$. base); HRMS calcd for C$_{15}$H$_{20}$N$_2$O+H: 245.1654. Found: 245.1675.

H. 1-Cyclopentyl-3-ethyl-1H-indazole-carbaldehyde. 106 mg (0.301 mmol, 0.05 equiv) tetrapropylammonium perruthenate (VII) were added to a room temperature suspension of 1.47 g (6.02 mmol, 1.0 equiv) (1-cyycyclopentyl-3-ethyl-1H-indazol-6-yl)methanol, 1.06 g (9.03 mmol, 1.5 equiv) N-methylmorpholine N-oxide and 3.01 g 4A molecular sieves in 12 mL anhydrous CH$_2$Cl$_2$. After 20 minutes the reaction mixture was filtered through a short column of silica gel (eluted with CH$_2$Cl$_2$). Fractions containing product were concentrated, and the residue chromatographed on a silica gel column (15% ethyl acetate/hexanes, flash) to give 924 mg (63% of a pale yellow solid: mp 41° C.; IR (KBr) 3053, 2966, 2872, 2819, 1695 cm$^{-1}$; $^1$H NMR (300 MHz, CDCl$_3$) δ 10.13 (s, 1H), 7.93 (d, 1H, J-0.9 Hz), 7.77 (d, 1H, J=8.4 Hz), 7.60 (dd, 1H, J=1 .2, 8.4 Hz), 5.00 (quintet, 1H, J=7.5 Hz), 3.01 (q, 2H, J=7.6 Hz), 2.2 (m, 4H), 2.0 (m, 2H), 1.7 (m, 2H), 1.39 (t, 3H, J=7.5 Hz); MS (Cl, NH$_3$) m/z 243 (M+H+, base); Anal. calcd for C$_{15}$H$_{18}$N$_2$O: C, 74.35; H, 7.49; N, 11.56. Found: C, 74.17; H, 7.58; N, 11.79.

PREPARATION 2

1-Cyclorentyl-3-ethyl-1H-indazole-6-carbaldehyde

A. 4-Bromo-2-nitro-1-propyl-benzene. 125 g (628 mmol, 1.0 equiv) 1-bromo-4-propyl-benzene were added in one portion to a 10° C. solution of 600 mL conc. H$_2$SO$_4$ and 200 mL H$_2$O. With vigorous mechanical stirring, an ambient temperature mixture of 43.2 mL (691 mmol, 1.1 equiv) conc. HNO$_3$ (69–71%, 16M) in 150 mL conc. H$_2$SO$_4$ and 50 mL H$_2$O was added dropwise over 30 minutes. The ice bath was allowed to warm to ambient temperature, and the reaction stirred at room temperature for 68 hours. The reaction mixture was poured into a 4 L beaker, loosely packed full with crushed ice. After stirring 1 hour, the mixture was transferred to a 4 L separatory funnel and extracted 4×800 mL isopropyl ether. The organic extracts were combined, washed 3×800 mL H$_2$O, 1×500 mL brine, and dried over Na$_2$SO$_4$. Filtration, concentration of filtrate and drying gave 150 mL of a yellow liquid, which was purified by silica gel chromatography (2 columns, 3 kg silica gel each, 2% ethyl acetate/hexanes) to afford 63.9 g (42%) of a yellow liquid. The desired regioisomer is the less polar of the two, which are formed in a 1:1 ratio. bp 108° C., 2.0 mm; IR (CHCl$_3$) 3031, 2966, 2935, 2875, 1531, 1352 cm$^{-1}$; $^1$H NMR (300 MHz, CDCl$_3$) δ 8.01 (d, 1H, J=2.1 Hz), 7.62 (dd, 1H, J=2.1, 8.3 Hz) 7.23 (d, 1H, J=8.3 Hz), 2.81 (m, 2H), 1.67 (m, 2H), 0.98 (t, 3H, J=7.4 Hz); $^{13}$C NMR (75.5 MHz, CDCl$_3$) a 13.94, 23.74, 34.43, 119.6, 127.4, 133.3, 135.7, 136.4, 149.8; GCMS (El) m/z 245/243 (M+.), 147 (base); HRMS calcd for C$_9$H$_{10}$NO$_2$Br+H: 243.9973. Found: 243.9954.

B. 5-Bromo-2-propyl-phenylamine. 121 g (639 mmol, 3.0 equiv) of stannous chloride (anhydrous) were added in one portion to a room temperature solution of 51.9 g (213 mmol, 1.0 equiv) 4-bromo-2-nitro-1-propyl-benzene in 1200 mL absolute ethanol and 12 mL (6 equiv) $H_2O$. After 24 hours at room temperature, most of the ethanol was removed on a rotary evaporator. The residue was poured into a 4 L beaker, ¾ full with crushed ice and $H_2O$. 150 g of NaOH pellets were added portionwise, with stirring, until the PH=10 and most of the tin hydroxide has dissolved. The mixture was divided in half, and each half extracted 2×750 mL ethyl acetate. All four ethyl acetate extracts were combined, washed 1×500 mL each 1N NaOH, $H_2O$, and brine, then dried over $Na_2SO_4$. Filtration, concentration of filtrate and drying gave a yellow liquid, which was purified on a 1.2 kg silica gel column (1:12 ethyl acetate/hexanes) to give 41.83 g (92%) of a pale yellow liquid: IR (CHCl$_3$) 3490, 3404, 3008, 2962, 2933, 2873, 1620, 1491 cm$^{-1}$; $^1$H NMR (300 MHz, CDCl$_3$) δ 6.8–6.9 (m, 3H), 3.90 (br s, 2H), 2.42 (m, 2H), 1.62 (m, 2H), 0.99 (t, 3H, J=7.3 Hz); GCMS (El) m/z 215/213 (M+.), 186/184 (base); Anal. calcd for $C_9H_{12}NBr$: C, 50.49; H, 5.65; N, 6.54. Found: C, 50.77; H, 5.70; N, 6.50.

C. 6-Bromo-3-ethyl-1H-indazole. 49.22 g (230 mmol, 1.0 equiv) 5-bromo-2propyl-phenylamine were placed in a 3 L flask and chilled in an ice bath. A 0° C. solution of 57.5 mL (690 mmol, 3.0 equiv) conc. HCl in 165 mL $H_2O$ was added, and the resulting solid mass which formed was ground up until a fine white suspension resulted. 100 mL more $H_2O$ were added, then a solution of 15.9 g (230 mmol, 1.0 equiv) sodium nitrite in 75 mL $H_2O$ was added dropwise over 10 minutes. The ice bath was removed, and the reaction allowed to stir at room temperature for 30 minutes. The reaction mixture was then filtered through a sintered glass funnel, precooled to 0° C. The filtrate was chilled in an ice bath, and with mechanical stirring, a 0° C. solution/suspension of 32.8 g (313 mmol, 1.36 equiv) ammonium tetrafluorobrate in 110 mL $H_2O$ was added dropwise over 10 minutes. The thick white suspension which formed (aryl diazonium tetrafluoroborate salt) was allowed to stir 1.5 hours at 0° C. The mixture was then filtered, and the solid washed 1×200 mL 5% aq. $NH_4BF_4$ (cooled at 0° C.), 1×150 mL $CH_3OH$ (cooled to 0° C.), then 1×200 mL $Et_2O$. Drying at high vacuum, ambient temperature for 1 hour gave 54.47 g (76%) of the diazonium salt, an off-white solid.

1500 mL of ethanol free chloroform were placed in a 3-neck flask, then 34.16 g (348 mmol, 2.0 equiv) potassium acetate (powdered and dried) and 2.3 g (8.7 mmol, 0.05 equiv) 18-crown-6 were added. After 10 minutes, the diazonium salt was added in one portion, and the reaction mixture allowed to stir at room temperature under nitrogen atmosphere for 18 hours. The mixture was then filtered, the solid washed 2× with CHCl$_3$, and the filtrate concentrated to give 47 g of crude product (brown crystals). Silica gel chromatography (1.2 kg silica gel, ethyl acetate/hexanes gradient 15%, 20%, 40%) gave 21.6 g (55% for second step, 42% overall) of tan crystals: mp 112–114° C.; IR (KBr) 3205, 3008, 2969, 2925, 1616, 1340, 1037 cm$^{-1}$; $^1$H NMR (300 MHz, CDCl$_3$) δ 9.86 (br s, 1H), 7.61 (d, 1H, J=1.3 Hz), 7.57 (d, 1H, J=8.4 Hz), 7.24 (dd, 1H, J=1.5, 8.6 Hz), 2.99 (q, 2H, J=7.6 Hz), 1.41 (t, 3H, J=7.6 Hz); MS (Cl, NH$_3$) m/z 227/225 (M+H$^+$, base); Anal. calcd for $C_9H_9N_2Br$: C, 48.02; H, 4.03; N, 12.45. Found: C, 48.08; H, 3.87; N, 12.45.

D. 6-Bromo-1-cyclopentyl-3-ethyl-1H-indazole. 2.46 g (61.4 mmol, 1.05 equiv) sodium hydride, 60% oil dispersion, were added in 0.5 g portions to a 100C solution of 13.17 g (58.5 mmol, 1.0 equiv) 6-bromo-3-ethyl-1H-indazole in 500 mL anhydrous DMF. The mixture was stirred at ambient temperature for 20 minutes, then a solution of 8.8 mL (81.9 mmol, 1.4 equiv) cyclopentyl bromide in 10 mL anhydrous DMF was added dropwise. After 18 hours, the reaction mixture was poured into 2 L $H_2O$ and extracted 2×1 L ethyl acetate. The organic extracts were combined, washed 2×750 mL $H_2O$, 1×500 mL brine, and dried over $Na_2SO_4$. Filtration, concentration of filtrate and drying gave 20.7 g of crude product, which was purified on a silica gel column (1.1 kg silica gel, 3% ethyl acetate/ hexanes) to give 10.6 g (62%) of an amber liquid: IR (CHCl$_3$) 2972, 2875, 1606, 1501, 1048 cm$^{-1}$; $^1$H NMR (300 mHz, CDCl$_3$) δ 7.56 (d, 1H, J=1.3 Hz), 7.52 (d, 1H, J=8.7 Hz), 7.17 (dd, 1H, J=1.5, 8.5 Hz), 4.83 (quintet, 1H, J=7.6 Hz), 2.96 (q, 2H, J=7.6 Hz), 2.15 (m, 4H), 2.0 (m, 2H), 1.65 (m, 2H), 1.36 (t, 3H, J=7.7 Hz); MS (thermospray, NH$_4$OAc) m/z 295/293 (M+H+, base); Anal. calcd for $C_{14}H_{17}N_2Br$: C, 57.35; H, 5.84; N, 9.55. Found: C, 57.48; H, 5.83; N, 9.90.

E. 1-Cyclopentyl-3-ethyl-1H-indazole-6-carbaldehyde. 11.6 mL (28.4 mmol, 1.0 equiv) n-BuLi, 2.45 M in hexanes, were added to a –78° C. solution of 8.32 g (28.4 mmol, 1.0 equiv) 6-bromo-1-cyclopentyl-3-ethyl-1H-indazole in 200 mL anhydrous THF. After 30 min. at –78° C., 8.8 mL (114 mmol, 4.0 equiv) anhydrous DMF were added dropwise, and the reaction mixture was allowed to stir an additional 30 minutes at –78° C. The mixture was warmed to room temperature over 1 hour, then 125 mL 1N HCl were added. After stirring for 10 minutes, most of the THF was removed on a rotary evaporator. The residue was diluted with 500 mL $H_2O$, and extracted 2×250 mL ethyl acetate. The organic extracts were combined, washed 1×100 mL $H_2O$, 1×100 mL brine, and dried over $Na_2SO_4$. Filtration, concentration of filtrate and drying gave a yellow oil, which was purified on silica gel column (15% ethyl acetate/hexanes, gravity) to give 4.70 g (68%) of a yellow crystalline solid: $^1$H NMR (300 MHz, CDCl$_3$) identical to the spectrum of the title compound from Preparation 1.

EXAMPLE 1

Racemic 4-(1-Cyclopentyl-3-ethyl-1H-indazol-6-yl)-pyrrolidine-2-one

A. 2-(1-Cyclopentyl-3-ethyl-1H-indazol-6-ylmethylene)-malonic acid diethyl ester A mixture of 3.74 g (15.4 mmol, 1.0 equiv) 1-cyclopentyl-3-ethyl-1H-indazole-6-carbaldehyde, 2.33 mL (15.4 mmol, 1.0 equiv) diethyl malonate, and 1.52 mL (15.4 mmol, 1.0 equiv) piperidine in 60 mL anhydrous toluene was heated to reflux. A dean-Stark trap was used to drive the reaction to completion. After 24 hours, the reaction mixture was cooled to room temperature and the toluene removed on a rotary evaporator. The residue was diluted with 500 mL ethyl acetate and washed 2×150 mL saturated aqueous NH$_4$Cl, 1×150 mL $H_2O$, 1×150 mL brine, and dried over $Na_2SO_4$. Filtration, concentration of filtrate and drying gave 6.87 g crude product, which was purified on a silica gel column (10% ethyl acetate/hexanes, flash) to give 3.01 g (51%) of a yellow oil: IR (CHCl$_3$) 2974, 2940, 2874, 1724, 1257 cm$^{-1}$; $^1$H NMR (300 MHz, CDCl$_3$) δ 7.87 (s, 1H), 7.63(d, 1H, J=8.4 Hz), 7.52 (s, 1H), 7.15 (dd, 1H, J=1.4, 8.4 Hz), 4.88 (quintet, 1H, J=7.6 Hz), 4.3 (m, 4H), 2.96 (q, 2H, J=7.6 Hz), 2.15 (m, 4H), 2.0 (m, 2H), 1.7 (m, 2H), 1.3 (m, 9H); MS (Cl, NH$_3$) m/z 385 (M+H$^+$, base); Anal. calcd for $C_{22}H_{28}N_2O_4$: C, 68.74; H, 7.34; N, 7.27. Found: C, 68.50; H, 7.15; N, 7.23.

B. 2-[Cyano-(1-cyclopentyl-3-ethyl-1H-indazol-6-yl)-methyl]-malonic acid diethyl ester. 375 mg (7.65 mmol, 1.0 equiv) sodium cyanide were added in one portion to room temperature solution of 2.94 g (7.65 mmol, 1.0 equiv) 2-(1-cyclopentyl-3-ethyl-1H-indazol-6-ylmethylene)-malonic acid diethyl ester in 50 mL absolute ethanol. After 14 hour room temperature, the reaction mixture was concentrated on a rotary evaporator and the residue diluted with 500 mL ethyl acetate. 200 mL H$_2$O were added, and the mixture acidified to pH 3 with 1N HCl. The layers were separated, and the organic layer was washed 1×100 mL H$_2$O, 1×100 mL brine, and dried over Na$_2$SO$_4$. Filtration, concentration of filtrate and drying gave an orange oil, which was purified on a silica gel column (15%–25% ethyl acetate/hexanes gradient) to give 2.84 g (90%) of a clear oil: IR (CHCl$_3$) 3032, 2974, 2941, 2875, 2250, 1752, 1736, 1244 cm$^{-1}$; $^1$H NMR (300 MHz, CDCl$_3$) δ 7.67 (d, 1H, J=8.4 Hz), 7.41 (s, 1H), 7.04 (dd, 1H, J=1.4, 8.4 Hz), 4.89 (quintet, 1H, J=7.6 Hz), 4.66 (d, 1H, J=9.5 Hz), 4.3 (m, 2H), 4.1 (m, 2H), 3.96 (d, 1H, J=9.5 Hz), 2.97 (q, 2H, J=7.6 Hz), 2.15 (m, 4H), 2.0 (m, 2H), 1.36 (t, 3H, J=7.5 Hz), 1.30 t, 3H, J=7.1 Hz), 1.06 (t, 3H, J=7.1 Hz); MS (Cl, NH$_3$) m/z 412 (M+H$^+$, base); Anal. calcd for C$_{23}$H$_{29}$N$_3$O$_4$: C, 67.13; H, 7.10; N, 10.21. Found: C, 67.29; H, 6.97; N, 10.06.

C. Racemic 4-(1-Cyclopentyl-3-ethyl-1H-indazol-6-yl)-pyrrolidine-2-one. 3.0 g platinum (IV) oxide and 35 mL acetic acid were placed on a Parr® hydrogenation apparatus and shaken under 45 psi H$_2$ at room temperature for 1 hour. 2.79 g (6.78 mmol, 1.0 equiv) 2-[cyano-(1-cyclopentyl-3-ethyl-1H-indazol-6-yl)-methyl]-malonic acid diethyl ester were added, dissolved in 40 mL acetic acid, then the mixture was shaken under 45 psi H$_2$ at room temperature for 3 hours. The reaction mixture was filtered through celite®, and the filtrate concentrated on a rotary evaporator and azeotroped 3× with toluene. Drying at high vacuum, room temperature gave 3.37 g of a yellow oil. This oil was dissolved in 100 mL toluene, 10 mL triethylamine were added, and the mixture heated to reflux under nitrogen atmosphere. After 17 hours, the reaction mixture was cooled to room temperature, and the toluene removed on a rotary evaporator. The residue was dissolved in 250 mL ethyl acetate and washed 3×50 mL 1N HCl, 1×50 mL H$_2$O, 1×50 mL brine, and dried over Na$_2$SO$_4$. Filtration, concentration of filtrate and drying gave 2.84 g of an amber oil. This second oil was dissolved in 60 mL ethanol and 20 mL 1N NaOH were added. After 30 minutes of reflux, the reaction mixture was cooled to room temperature and concentrated on a rotary evaporator. The residue was diluted with 200 mL H$_2$O, acidified to pH=2 with 1N HCl, and extracted 2×100 mL ethyl acetate. The organic extracts were combined, washed 1×50 mL H$_2$O, 1×50 mL brine, and dried over Na$_2$SO$_4$. Filtration, concentration of filtrate and drying brine, and dried over Na$_2$SO$_4$. Filtration, concentration of filtrate and drying gave 2.45 g of a tan amorphous solid. This solid was heated in an oil bath to 180° C. (external) under nitrogen atmosphere. After 20 minutes at 180° C., all bubbling had ceased, and the brown liquid which formed was cooled to room temperature. As it cooled, it crystallized as a tan solid. Silica gel chromatography (5% CH$_3$OH/CH$_2$Cl$_2$, flash) gave 1.41 g of a white solid, which was recrystallized from ethyl acetate/hexanes to give 1.21 g (60% overall) white silvery flakes: mp 197–198° C.; IR (KBr) 3197, 3093, 2967, 2874, 2818, 1705, 1682 cm$^{-1}$; $^1$H NMR (300 MHz, CDCl$_3$) δ 7.65 (d, 1H, J=8.2 Hz), 7.23 (s, 1H), 6.99 (dd, 1H, J=1.4, 8.3 Hz), 6.09 (br s, 1H), 4.89 (quintet, 1H, J=7.7 Hz), 3.85 (m, 2H), 3.5 (m, 1H), 2.97 (q, 2H, J=7.6 Hz), 2.85 (m, 1H), 2.55 (m, 1H), 2.14 (m, 4H), 2.0 (m, 2H), 1.7 (m, 2H), 1.37 (t, 3H, J=7.5 Hz); MS (Cl, NH$_3$) m/z 298 (M+H$^+$, base); Anal. calcd for C$_{19}$H$_{23}$N$_3$O: C, 72.69; H, 7.80; N, 14.13. Found: C, 72.39; H, 7.84; N, 14.33.

EXAMPLE 2

(+)-4-(1-Cyclopentyl-3-ethyl-1H-indazol-6-yl)-pyrrolidine-2-one and (−)-4-(1-cyclopentyl-3-ethyl-1H-indazol-6-yl)-pyrrolidine-2-one 958 mg of racemic 4-(1-cyclopentyl-3-ethyl-1H-indazol-6-yl)-pyrrolidine-2-one were resolved chromatographically on a 5 cm id×50 cm long Chiracel OD column. The mobile phase was 88:12 heptane:isopropanol with 0.05% diethylamine as additive. The feed for each cycle was 60 mg racemate in 4 mL isopropanol. The flow rate was 70 mL/min and the separation was monitored at 230 nm. The two peaks eluted at 50 and 55 minutes. The heart cuts of the 50 and 55 minutes. The heart cuts of the 50 minutes peak were pooled and assayed at 96% ee. This fraction (8L) was concentrated, and the residue purified on a silica gel column (5% CH$_3$OH/CH$_2$Cl$_2$, flash) to give 371 mg of a white solid, which was recrystallized from ethyl acetate/hexanes to give 295 mg of silvery-white flakes: mp 132–135° C.; IR (KBr) 3204, 3097, 2967, 2873, 1702 cm$^{-1}$; $^1$H NMR (300 MHz, CDCl$_3$) δ 7.65 (d, 1H, J=8.4 Hz), 7.23 (s, 1H), 6.99 (dd, 1H, J=1.2, 8.3 Hz), 5.94 (br s, 1 H0, 4.89 (quintet, 1H, J=7.6 Hz), 3.85 (m, 2H), 3.49 (m, 1H), 2.98 (q, 2H, J=7.7 Hz), 2.8 (m, 1H), 2.6 (m, 1H), 2.2 (m, 4H), 2.0 (m, 2H), 1.7 (m, 2H), 1.37 (t, 3H, J=7.4 Hz); MS (Cl, NH$_3$) m/z 298 (M+H$^+$, base); Anal. calcd for C$_{18}$H$_{23}$N$_3$O: C, 72.69; H, 7.80; N, 14.13. Found: C, 72.41; H, 7.87; N, 14.17; [a]D=−34.3° C. (c=1.15, CHCl$_3$). The heart cuts of the 55 minutes peak were pooled and assayed at 94% ee. This fraction (13 L) was concentrated, and the residue purified on a silica gel column (5% CH$_3$OH/CH$_2$/Cl$_2$ flash) to give 400 mg of a white solid, which was recrystallized from ethyl acetate/hexanes to give 256 mg of white crystals: mp 132.5–135.5° C.; IR (KBr) 3203, 3097, 2967, 2872, 1703 cm$^{-1}$; $^1$H NMR (300 MHz, CDCl$_3$) δ 7.65 (d, 1H, J=8.4 Hz), 7.23 (s, 1H), 6.99 (dd, 1H, J=1.2, 8.3 Hz), 5.94 (br s, 1H), 4.89 (quintet, 1H, J=7.6 hz), 3.85 (m, 2H), 3.49 (m, 1H), 2.98 (q, 2H, J=7.7 Hz), 2.8 (m, 1H), 2.6 (m, 1H), 2.2 (m, 4H), 2.0 (m, 2H), 1.7 (m, 2H), 1.37 (t, 3H, J=7.4 Hz); MS (Cl, NH$_3$) m/z 298 (M+H$^+$, base); Anal. calcd for C$_{18}$H$_{23}$N$_3$O: C, 72.69; H, 7.80; N, 14.13. Found: C, 72.76; H, 7.94; N, 14.20; [a]D=+32.9° (c=1.19, CHCl$_3$).

What is claimed is:
1. A compound of Formula (I):

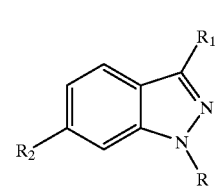

or a pharmaceutically acceptable salt thereof, wherein:

R is H; (C$_1$–C$_6$) alkyl; or —(CH$_2$)$_m$(C$_3$–C$_7$) cycloalkyl, where m is 0 to 2; wherein said R groups are optionally substituted by one or more substituents independently selected from the group consisting of halo; hydroxy; (C$_1$–C$_5$) alkyl; (C$_2$–C$_5$) alkenyl; (C$_{:1}$–C$_5$) alkoxy; (C$_3$–C$_6$) cycloalkoxy; trifluoromethyl; nitro; —CO$_2$R$_{10}$; —C(=O)NR$_{10}$R$_{11}$; —NR$_{10}$R$_{11}$; and —SO$_2$NR$_{10}$R$_{11}$;

R$_1$ is H; (C$_1$–C$_7$) alkyl; (C$_2$–C$_3$) alkenyl; phenyl; (C$_3$–C$_7$) cycloalkyl; or (C$_3$–C$_7$) cycloalkyl(C$_1$–C$_2$) alkyl; wherein said alkyl, alkenyl and phenyl R$_1$ groups are optionally substituted by 1 to 3 substituents independently selected from the group consisting of methyl; ethyl; trifluoromethyl; and halo;

R$_2$ is a 2-oxo-4-pyrrolyl group of Formula (Ia)$_1$:

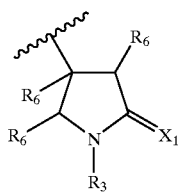

wherein:

X$_1$ is O or S;

R$_3$ is H; hydroxy; (C$_1$–C$_4$) alkoxy; —CHR$_7$(O)$_q$(CH$_2$)$_m$A where q is 0 or 1, m is 0 to 2, and A is phenyl optionally substituted by 1 or 2 R$_{14}$ groups or by 1 R$_{15}$ group; and R$_6$ is in each instance independently selected from the group consisting of H or halo one of —R$_6$ represents cyano; R$_{13}$; cyclopropyl optionally substituted by R$_9$; —OR$_{10}$; —CH$_2$OR$_{10}$; —NR$_{10}$R$_{12}$; —CH$_2$NR$_{10}$R$_{12}$; —C(O)OR$_{10}$; —C(O)NR$_{10}$R$_{12}$; —CH═CR$_9$R$_{10}$; —C(O)CR$_9$; and —C(═Z$_3$)H;

wherein with respect to the above substituent groups:

R$_7$ is H; or —C(O)R$_8$;

R$_8$ is independently selected from the group consisting of —OR$_{10}$; —NR$_{10}$R$_{12}$; and R$_{13}$;

R$_9$ is in each instance independently selected from the group consisting of H; halo; and (C$_1$–C$_4$) alkyl optionally substituted by 1 to 3 fluorines;

R$_{10}$ and R$_{11}$ are in each instance independently selected from the group consisting of H; and (C$_1$–C$_4$) alkyl;

R$_{12}$ is in each instance independently selected from the group consisting of —OR$_{10}$; and R$_{10}$;

R$_{13}$ is (C$_1$–C$_4$) alkyl;

R$_{14}$ is independently selected from the group consisting of halo; nitro; cyano; —NR$_{10}$R$_{16}$; —NR$_{16}$R$_{12}$; —C(═Z$_3$)R$_8$, —S(O)$_m$R$_{13}$ where m is 0 to 2; —OR$_{12}$; —OC(O)NR$_{10}$R$_{12}$; —C(NR$_{12}$)NR$_{10}$R$_{12}$; —C(NR$_{10}$)SR$_{13}$; —OC(O)CH$_3$, —C(NCN)NR$_{10}$R$_{12}$; —C(S)NR$_{10}$R$_{12}$; —NR$_{12}$C(O)R$_{17}$; and —C(O)R$_{17}$;

R$_{15}$ is independently H; or (C$_1$–C$_4$) alkyl optionally substituted by 1 to 3 fluorines;

R$_{16}$ is in each instance independently selected from the group consisting of H; R$_{13}$; —C(O)R$_{13}$; —C(O)C(O)R$_8$; —C(O)NR$_{10}$R$_{12}$; —S(O)$_m$R$_{13}$ where m is 0 to 2; —C(NCN)SR$_{13}$; —C(NCN)R$_{13}$; —C(NR$_{12}$)R$_{13}$; —C(NR$_{12}$)SR$_{13}$; and —C(NCN)NR$_{10}$R$_{12}$;

R$_{17}$ is independently R$_{13}$; or —C(O)R$_{13}$; and

Z$_3$ is in each instance independently selected from the group consisting of O; NR$_{12}$; NOR$_{10}$; N(CN); C(CN)$_2$; CR$_{10}$NO$_2$; CR$_{10}$C(O)OR$_{13}$; CR$_{10}$C(O)NR$_{10}$R$_{11}$; C(CN)NO$_2$; C(CN)C(O)OR$_{13}$; and C(CN)C(O)NR$_{10}$R$_{11}$.

2. A compound according to claim 1 wherein R is cyclopentyl or cyclohexyl; R$_1$ is (C$_1$–C$_2$) alkyl; and R$_2$ is a substituent of Formula (Ia)$_1$ wherein X$_1$ is O, and R$_3$ and R$_6$ are both H.

3. A compound of claim 1 selected from the group consisting of:

racemic 4-(1-Cyclopentyl-3-ethyl-1H-indazol-6-yl)-pyrrolidine-2-one;

(+)-4-(1-Cyclopentyl-3-ethyl-1H-indazol-6-yl)-pyrrolidine-2-one;

(−)-4-(1-Cyclopentyl-3-ethyl-1H-indazol-6-yl)-pyrrolidine-2-one;

or a pharmaceutically acceptable salt thereof.

4. A compound of claim 1 selected from the group consisting of:

racemic 4-(1-Cyclohexyl-3-ethyl-1H-indazol-6-yl)-pyrrolidine-2-one;

(+)-4-(1-Cyclohexyl-3-ethyl-1H-indazol-6-yl)-pyrrolidine-2-one;

(−)-4-(1-Cyclohexyl-3-ethyl-1H-indazol-6-yl)-pyrrolidine-2-one;

or a pharmaceutically acceptable salt thereof.

5. A compound of claim 1 wherein R$_2$ is a substituent of Formula (Ia), wherein X$_1$ is O.

6. The compound of claim 5 wherein R is cyclohexyl or cyclopentyl.

7. The compound of claim 6 wherein R$_1$ is C$_1$–C$_2$ alkyl optionally substituted by 1 to 3 fluorines.

8. The compound of claim 7 wherein R$_1$ is ethyl.

9. A pharmaceutical composition for the inhibition of phosphodiesterase (PDE) type IV or the production of tumor necrosis factor (TNF) in a mammal comprising a therapeutically-effective amount of a compound of claim 1 and a pharmaceutically acceptable carrier.

10. A method of treating asthma in a mammal in need of such treatment by inhibiting phosphodiesterase (PDE) type IV or the production of tumor necrosis factor (TNF) in said mammal, which comprises administering to said mammal a therapeutically effective amount of a compound of claim 1.

11. A pharmaceutical composition for the treatment of asthma in a mammal in need of such treatment, comprising a therapeutically effective amount of a compound of claim 1 and a pharmaceutically acceptable carrier.

12. A method of treating asthma in a mammal in need of such treatment, which comprises administering to said mammal a therapeutically effective amount of a compound of claim 1.

* * * * *